(12) United States Patent
Steiner et al.

(10) Patent No.: US 6,410,043 B1
(45) Date of Patent: Jun. 25, 2002

(54) METHOD FOR CHEMOPREVENTION OF PROSTATE CANCER

(75) Inventors: Mitchell S. Steiner, Germantown; Sharan Raghow, Collierville, both of TN (US)

(73) Assignee: The University of Tennessee Research Corporation, Knoxville, TN (US)

( * ) Notice: Subject to any disclaimer, the term of this patent is extended or adjusted under 35 U.S.C. 154(b) by 0 days.

(21) Appl. No.: 09/660,191

(22) Filed: Sep. 12, 2000

Related U.S. Application Data

(63) Continuation-in-part of application No. 09/531,472, filed on Mar. 20, 2000, which is a continuation-in-part of application No. 09/436,208, filed on Nov. 8, 1999, which is a continuation-in-part of application No. 09/306,958, filed on May 7, 1999.
(60) Provisional application No. 60/084,602, filed on May 7, 1998.

(51) Int. Cl.[7] ............................ A61F 13/00; A61K 9/14; A61K 9/20; A61K 9/48
(52) U.S. Cl. ...................... 424/422; 424/434; 424/489; 424/464; 424/433; 424/452; 514/944; 514/965; 514/938
(58) Field of Search .................. 424/489, 434, 424/464, 422, 433, 452; 514/648, 408, 944, 965, 938

(56) References Cited

U.S. PATENT DOCUMENTS

| | | | |
|---|---|---|---|
| 4,329,364 A | | 5/1982 | Neri et al. |
| 4,474,813 A | | 10/1984 | Neri et al. |
| 4,696,949 A | | 9/1987 | Toivola et al. |
| 4,990,538 A | | 2/1991 | Harris et al. |
| 5,491,173 A | * | 2/1996 | Toivola et al. ............... 514/648 |

(List continued on next page.)

FOREIGN PATENT DOCUMENTS

| | | |
|---|---|---|
| EP | 415 623 A2 | 3/1991 |
| EP | 616 529 B1 | 9/1994 |
| EP | 095875 | 12/1995 |
| WO | 94/12162 | 6/1994 |
| WO | 95/26720 | 10/1995 |
| WO | 9608046 A1 | 3/1996 |
| WO | 98/58634 | 12/1998 |
| WO | WO-99/56739 | * 11/1999 |
| WO | 0008001 | 2/2000 |
| WO | 0047214 | 8/2000 |

OTHER PUBLICATIONS

Bostwick, "Prostatic Intraepithelial Neoplasia and Atypical Adenomatous Hyperplasia," Prospective Origins of Prostate Carcinoma, 1996, p. 330–336.*

(List continued on next page.)

Primary Examiner—Thurman K. Page
Assistant Examiner—Blessing Fubara
(74) Attorney, Agent, or Firm—Eitan, Pearl, Latzer & Cohen-Zedek; Mark S. Cohen

(57) ABSTRACT

This invention provides the chemoprevention of prostate cancer and, more particularly, to a method of preventing prostate carcinogenesis comprising the steps of administering to a human subject having a precancerous precursor of prostate adenocarcinoma, a pharmaceutical preparation comprising a chemopreventive agent to prevent, prevent recurrence of, suppress or inhibit prostate carcinogenesis. The present invention provides a safe and effective method for suppressing or inhibiting latent prostate cancer and is particularly useful for treating subjects having elevated risk of developing prostate cancer, for example, those having benign prostatic hyperplasia, prostate intraepithelial neoplasia (PIN), or an abnormally high level of circulating prostate specific antibody (PSA), or who have a family history of prostate cancer.

17 Claims, 6 Drawing Sheets

U.S. PATENT DOCUMENTS

| | | | |
|---|---|---|---|
| 5,571,534 A | 11/1996 | Jalonen et al. | |
| 5,595,722 A | 1/1997 | Grainger et al. | |
| 5,595,985 A | 1/1997 | Lubrie | |
| 5,599,844 A | 2/1997 | Grainger et al. | |
| 5,605,700 A | 2/1997 | DeGregorio et al. | |
| 5,629,007 A | 5/1997 | Audia et al. | |
| 5,635,197 A | 6/1997 | Audia et al. | |
| 5,650,425 A * | 7/1997 | Biegnon et al. | 514/408 |
| 5,788,964 A | 8/1998 | Baral et al. | |

OTHER PUBLICATIONS

Martin R. Schneider et al. "Nonsteroidal Antiestrogens and Partial Estrogens with Prostatic Tumor Inhibiting Activity", Cancer Research Clinical Oncology Springer–Verlag 1986, J Cancer Res Clin Oncol (1986) 112:258–265, pp. 258–265.

Celine Martel et al. "Binding Characteristics of Novel Nonsteroidal Antestrogens to the Rat Uterine Estrogen Receptors", Pergamon, J. Steroid Biochem. Molec. Bio., vol. 64, No. 3–4, pp. 199–205, 1998.

Ritva Valavaara, MD, PhD "Reliability of Estrogen Receptors in Predicting Response To Antiestrogens", Oncology, vol. 11 No. 5 Supplement No. 4 pp. 14–18.

Richard Gams, MD "Phase III Trials of Toremifene vs Tamoxifen" Oncology vol. 11, No. 5, Supplement 4, May 1997.

Christian Rohlff et al. "Prostate Cancer Cell Growth Inhibition by Tamoxifen Is Associated With inhibition of Protein Iinase C and Induction of p21" The Prostate 37:51–59 (1998) ©1998 Wiley–Liss, Inc.

Nevalanine et al. "Hormone Regulation of Human Prostate in Organ Culture" Cancer Ress, vol. 53, No. 21, 1993, pp. 5199–5207, XO002117653.

Greenwald "Expanding Horizons in Breast and Prostate Cancer Prevention and Early Detection", in J. Cancer Education, 1993, vol. 8, No. 2, pp. 91–107.

Brawley et al., "Chemoprevention of Prostate Cancer" in Urology, 1994, vol. 43, No. 5.

Kelloff et al., "Introductory Remarks: Development of Chemopreventive Agents for Prostate Cancer" in Journal of Cellular Biochemistry, 1992, Supplement 16H: 1–8.

Lucia et al., "Chemopreventive Activity of Tamoxifen, N–(4–Hydroxyphenyl)retinamide, and the Vitamin D Analogue Ro24–553 1 for Androgen–promoted Carcinomas of the Rat Seminal Vesicle and Prostate" in Cancer Research, 1995, vol. 55, pp. 5621–5627.

Potter et al., "A Mechanistic Hypothesis for DNA Adduct Formation By Tamoxifen Following Hepatic Oxidative Metabolism" in Carcinogenesis, 1994, vol. 15, No. 3, pp. 439–442.

Gingrich et al., "Androgen–independent Prostate Cancer Progression in the Tramp Model", in Cancer Research 57, Nov. 1, 1997, pp. 4687–4691.

Gingrich et al., "Pathologic Progression of Autochthonous Prostate Cancer in the Tramp Model", Prostate Cancer and Prostatic Diseases, 1999, 2, pp. 70–75.

Gingrich et al., "Metastatic Prostrate Cancer in a Transgenic Mouse", in Cancer Research 56, Sep. 15, 1996, pp. 4096–4102.

Gershanovich et al., "A Phase III Comparison of Two Toremifene Doses to Tamoxifen in Postmenopausal Women with Advanced Breast Cancer", Breast Cancer Research and Treatment 45, 1997, pp. 251–262.

Hayes et al. "Randomized Comparison of Tamoxifen and Two Separate Doses of Toremifenein Postmenopausal Patients with Metastatic Breast Cancer", Journal of Clinical Oncology, vol. 13, No. 10, 1995, pp. 2556–2566.

Pyrhönen et al., "Comparison of Toremifene and Tamoxifen in Postmenopausal Patients with Advanced Breast Cancer: a Randomized Double–blind, the 'Nordic' Phase III Study", British Journal of Cancer, 1997, 76(2), pp. 270–277.

Neubauer et al., "Endocrine and Antiprostatic Effects of Raloxifene (LY156758) in the Male Rat", The Prostate 23, 1993, pp. 245–262.

Pollard, "Prevention of Prostate–Related Cancers in Lobund–Wistar Rats", The Prostate 39, 1999, pp. 305–309.

Simard et al., "Keoxifene Shows Pure Antiestrogenic Activity in Pituitary Gonadotrophs", Molecular and Cellular Endocrinology 39, 1985, pp. 141–144.

Perry "High Dose Toremifene for Estrogen and Progesterone Receptor Negative Metastatic Breast Cancer: a Phase II Trial of the Cancer and Leukemia Group B (CALGB)", in Breast Cancer Res Treat—1995; 26(1): 25–40.

Hietanen T "Open Phase II Study of High–Dose Toremifene as First–Line Therapy for Advanced Breast Cancer" in Oncology—May 1997; 11(5 Suppl 4): 37–40.

Black et al. "Uterine Bioassay of Tamoxifen, Trioxifene and a New Estrogen Antogonist (LY117018) in Rats and Mice" in Life Sciences, 1980, vol. 26, pp. 1453–1458.

Moore et al. "Regulation of Cytoplasmic Dihydrotestosterone Binding in Dog Prostate by 17β–Estadiol", in J. Clin. Invest. © The American Society for Clinical Investigation, Inc., vol. 63 Mar. 1979, pp. 351–357.

Shirai et al. "Effects of Testosterone, Dihydrotestosterone and Estrogen on 3,2'–Dimethyl–4–Aminobiphenyl–Induced Rat Prostate Carcinogenesis" in Int. J Cancer: 57, 224–228 (1994).

Greenwald et al. "Breast Cancer Prevention and Early Detection", pp. 93–106.

Shenfeld et al. "Androgen Deprivation Therapy", Chapter 37, Section III/Prostate Cancer, pp. 467–477.

Jordan VC "Toremifene As An Anticancer Agent", Cancer Invest 1990; 8(2)271.

Karlsson S. et al. "A Two–Year Dietary Carcinogenicity Study Of The Antiestrogen Toremifene In Sprague–Dawley Rats" Drug Chem Toxicol 1996 Nov; 19(4): 245–66.

Powles TJ "Status Of Antiestrogen Breast Cancer Prevention Trials" Oncology (Hunting) 1998 Mar; 12(3 Suppl 5): 28–31.

Moon RC et al. "Chemoprevention of MNU–Induced Mammary Tumorigenesis by Hormone Response Modifiers: Toremifene, RU 16117, Tamoxifen, Aminoglutethimide and Progesterone", Anticancer Res 1994 May–Jun.; 14(3A): 889–93.

Nevalainen MT et al. "Expression and Hormone Regulation Of Prolacting Receptors in Rat Dorsal and Lateral Prostate", Endocrinology 1996 Jul.; 137(7):3078–88

Foekens JA et al. "Expression Of Prostate–Specific Angtigen (PSA) Correlates With Poor Response To Tamoxifen Therapy In Recurrent Breast Cancer", Br J Cancer 1999 Feb.; 79(5–6): 888–94.

Brandes LJ et al. "Salutary Clinical Response Of Prostate Cancer To Antiandrogen Withdrawal: Assessment Of Flutamide In An In Vitro Paragdigm Predictive Of Tumor Growth Enhancement", Clin Cancer Res 1997 Aug.; 3(8): 1357–61.

Miyata E et al. "Effects Of Tamoxifen, An Antiestrogen, On Rat Prostate Carcinogenesis by 3,2'–Dimethyl–4–Aminobiphenyl And Testerone Do Not Support An Estrogen Role In Testerone Promotion", Prostate 1997 Apr. 1;31(1)9–13.

Pienta KJ et al. "A Phase II Evaluation Of Oral Tamoxifen And Intermittent Intravenous Vinblastine In Hormone–Refractory Adenocarcinoma Of The Prostate"., Am J Clin Oncol 1996 Oct.; 19(5):500–3.

Pienta KJ et al. "Inhibition Of Prostate Cancer Growth By Vinblastine And Tamoxifen", Prostate1995 May; 26(5): 270–4.

Lippman SM et al, "Cancer Chemoprevention", J. Clin Oncol 1994 Apr.; 12(4):851–73.

Szarka CE et al. "Chemoprevention Of Cancer", Curr Probl Cancer 1994 Jan.–Feb.; 18(1)–6–79.

Yu H et al. "Induction Of Prostate Specific Antigen Production By Steroids And Taxoxifen In Breast Cancer Cell Lines", Breast Cancer Res Treat 1994: 32(3)291–300.

Horton J et al. "Tamoxifen In Advanced Prostate Cancer: An ECOG Pilot Study", Prostate 1988; 12(2):173–7.

Kangas L "Development and Biochemical Pharmacology Of Toremifene, An Antiestrogenic Antitumor Drug", Acta Obstet Gynecol Scand 1991; 70(4–5):399.

Antila M et al. "Pharmacokinetics Of The Novel Antiestrogenic Agent Toremifene In Subjects With Altered Liver And Kidney Function" Clin Pharmacol Ther 1995 Jun.; 57(6):628–35.

Kamat AM et al. "Chemoprevention Of Urological Cancer", The Journal Of Urology, vol. 161, 1748–1760. Jun. 1999, pp. 1748–1760.

Ficton SA "Potential New Antiestrogens For The Treatment Of Breast Cancer", Highlights in Oncology Practice vol. 15, No. 2, 1997 pp. 47–52.

Nevalainen M. T. et al, "Estrogen and Prolactin Regulation of Rat Dorsal and Lateral Prostate in Organ Culture", Endocrinology, vol. 129, No. 2 pp. 612–619.

Moon R.C. et al. "Chemoprevention of MNU–Induced Mammary Tumorigenesis by Hormone Response Modifiers: Toremifene, RU 16117, Tamoxifen, Aminoglutethimide and Progesterone", Anticancer Research 14: 889–894 (1994).

Price K. R. et al. "Naturally Occurring Oestrogens in Food—A Review", Food Additives and Contaminants, 1985, vol. 2, No. 2, 73–106.

Prins Gail S. "Developmental Estrogenization Of The Prostate Gland", Prostate;Basic and Clinical Aspects pp. 245–263 (1997).

Kuiper George G. J. M. "Cloning Of A Novel Estrogen Receptor Expressed In Rat Prostate And Ovary", Proc. Natl. Acad. Sci USA vol. 93, pp. 5925–5930, Jun. 1996 Biochemistry.

Kulper George G. J. M. "Interaction Chemicals and Phytoestrogens With Estrogen Receptor β", Endocrinolgoy vol. 139, No. 10 (1998).

Horton John et al. "Tamoxifen In Advanced Prostate Cancer An ECOG Pilot Study", The Prostate 12: 173–177 (1988).

Hayes "A Randomized Comparison Of Tamoxifen, Trioxifene And A New Estrogen Antagonist (LY117018) In Rats Aand Mice" In Life Sciences, 1980, vol. 26, pp. 1453–1458.

Dhar JD et al. "Estrogen, Androgen and Antiestrogen Responses In The Accessory Organs Of Male Rats During Different Phases Of Life", Endocr Res 1998 May; 24(2): 159–69.

West Neal B et al. "Estrogen and Progestin Receptors And Aromatase Activity In Rhesus Monkey Prostate" Endocrinology, vol. 1, 123, (1998).

Strauss L "Genistein Exerts Estrogen–Like Effects in Male Mouse Reproductive Tract", Molecular and Cellular Endocrinology 144 (1998)83–93, Elsevier Science Ireland Ltd.

Strom Sara S. et al. "Phytoestrogen Intake and Prostate Cancer; A Case–Control Study Using a New Database", Nutrition and Cancer, 33(1), 20–25), (1999).

Kellof GJ et al., "Strategies For Chemoprevention Of Prostate Cancer", Prostate Cancer and Prostate Disease (1988) 5, 107.

Buelke–Sam Judy et al. "The Selective Estrogen Receptor Modulator, Realoxifene; An Overview Of Nonclinical Pharmacology and Reproductive Development Testing", Reproductive Toxicology vol. 12, No. 3 pp. 217–221, 1998.

Hobisch Alfred "Metastatic Lesions From Prostate Cancer Do Not Express Oestrogen and Progesterone Receptors" J. Pathol. 182: 356–361, 1997.

Albert David S. et al. "An Overview Of Clinical Cancer Chemoprevention Studies With Emphasis On Positive Phase III Studies" Overview of Diet Cancer 6928–6975 (1995).

Cheng E et al. "Endocrinology Of The Prostate", Prostate Diseases, chapter 5– pp. 57–71.

Bonkhoff H et al. "Estrogen Receptor Expression In Prostate Cancer and Premalignant Prosatic Lesions", American Journal of Paibology, vol. 155, No. 2 Aug. 1999.

"New Research Approaches In The Prevention and Cure Of Prostate Cancer", American Association For Cancer Research.

Xiaolin Zi et al. Silibinin Decreases Prostate–Specific Antigen With Cell Growth Inhibition Via G1 Arrest, leading To Differentiation Of Prostate Carcinoma Cells: Implications For Prostate Cancer Intervention:, Proc. Nsil. Acad. Sci, USA vol. 96, pp. 7490–7495, Jun. 1999, Medical Sciences.

Landstrom M, et al. Inhibitory Effects Of Soy and Rye Diets On The Development of Dunning R3327 Prostate Adenocarcinoma in Rats, The Prostate 36: 151–161 (1998).

Buelke–Sam J. et al. "The Selective Estrogen Receptor Modulator, Raloxifene: An overview Of NonClinical Pharmacology And Reproductive And Development Testing", Reprod Toxicol 1998 May–Jun.; 12(3):271–21.

Treinen KA et al. An Evaluation Of The Novel Selective Estrogen Receptor Modulator, Idoxifene, For Effects On Reproduction In Rats And Rabbits;, Toxicol Sci 1998 Feb.; 41(2):199–207.

Boehm S et al. "Estrogen Suppression As A Pharmacotherapeutic Strategy In The Medical Treatment Of Benign Prostatic Hyperplasia: Evidence For Its Efficacy From Stuides With Mepartricin" Wien Klin Wochenschr 1998 Dec. 11; 110(23):817–23.

Bergan RC et al. "A Phase II Study Of High–Dose Tamoxifen In Patients With Hormone–Refractory Prostate Cancer." Clin Cancer Res 1999 Sep.; 5(9):2366–73.

Chang William Y et al. "Estrogen Receptor–β: Implications For The Prostate Gland" The Prostate 40:115–124 (1999).

Shughrue Paul J. et al. "Comparative Distribution Of Estrogen Receptor–α (Er–α) And β (ER–β) mRNA In The Rat Pituitary, Gonad, And Reproductive Tract" Steroids 63: 498–504, 1998, Elsevier Science Inc.

Prins Gail S. et al, "Neonatal Estrogen Exposure Up–Regulates Estrogen Receptor Expression In The Developing And Adult Rat Prostate Lobes", Endocrinology 138: 1801–1809, 1997).

Hempstock J. et al. "Growth Inhibition Of Prostate Cell Lines In Vitro By Phyto–Oestrogens", British Journal Of Urology (1998), 82. 560–563.

Awoniyi Caleb A. et al. "Neonatal Exposure To Coumestro, A Phystoestrogen, Does Not Alter Spermatogenic Potential In Rats", Endocrine, vol. 7, No. 3, 337–341, Dec. 1997.

"Chemoprevention Of Prostate Cancer: Guidelines for Possible Intervention Strategies", Journal of Cellular Biochemistry, Supplement 16H:140–145 (1992).

"When Is Intervention Warranted?", Journal of Cellular Biochemistry, Supplement 16H:138–139 (1992).

"Editorial: A New Actor In The Estrogen Receptor Drama–Entre ER–β", Endocrinology vol. 138, No. 3, (1997).

Kuiper George G. J. M. et al. "Comparison Of The Ligand Binding Specificity And Transcript Tissue Distribution Of Estrogen Receptors α and β", Endocrinology vol. 138, No. 3, 863–870 (1997).

Colletta Anthony A. et al. "Alternative Mechanisms Of Action Of Anti–Oestrogens" Breast Cancer Research and Treatment 31: 5–9, 1994.

Griffiths K. et al. "Further Insights Into Endocrine Disease—Diet and Prostate Disease" An IPHC Teaching Programme.

Boyle, P. et al. "Epidemiology of Prostate Cancer Chemoprevention" Genetic and Environmental Factors In Prostate Cancer Genesis, European Urology 1989; 35; pp. 270–376.

Lancet Conference "The Challenge of Breast Cancer" Brugge 1994.

Mobbs B. G. et al. "Concentration and Cellular Distribution of Androgen Receptor In Human Prostatic Neoplasia: Can Estrogen Treatment Increase Androgen Receptor Content?"J. Steriod Biochem. vol. 19, No. 3, pp. 1279–1290, 1983.

Jordan Craig V, "Antiestrogenic Action of Raloxifene and Tamoxifen: Today and Tomorrow" Journal of the National Cancer Institute, vol. 90, No. 13, Jul. 1, 1998.

Hard Gordon C. et al. "Major Difference In the Hepatocarcinogenicity and DNA Adduct Forming Ability between Toremifene and Tamoxifen In Female Crl: CD(BR) Rats1", Cancer Research 53, 4534–4541, Oct. 1, 1993.

Bostwick, M.D. "Prostatic Intraepithelial Neoplasia and Atypical Adenomatous Hyperplasia", Prospective Origins of Prostate Carcinoma, 1996 American Cancer Socity, pp. 330–336.

Wari, Annl M. et al. "Apoptosis In Toremifene–Induced Growth Inhibition of Human Breast Cancer Cells In Vivo and In Vitro", Journal of the National Cancer Institute, vol. 85, No. 17, Sep. 1, 1993, pp. 1412–1418.

Zaridze David G. et al. "International Trends In Prostatic Cancer", Int. J. Cancer: 33, 223–230 (1984).

Bostwick David G. et al. "Reversibility of Prostatic Intraepithelial Neoplasia: Implications for Chemoprevention" Surrogate Endpoint Blomarkers for Clincal Trials of Prostate Cancer Chemoprevention, European Urology 1999.

Kelloff, Gary J. "Chemoprevention of Prostate Cancer: Concepts and Strategies", European Urology 1989; 35: 342–350.

Leav Irwin et al. "Androgen–Supported Estrogen–Enhanced Epithelial Proliferation In the Prostaets of Intact Noble Rats", The Prostate 15:23–40 (1989).

Rohliff C et al. "Prostate Cancer Cell Growth Inhibition by Tamoxifen is Associated With Inhibition of Protein Kinase C and Induction of p21 $^{wsI1/dp1}$", The Prostate 37: 51–59 (1998).

Kellen J. A. "The Effect of Toremifene on the Expression of Genes In a Roat Mammar Adenocarcinoma", In Vivo 10: 511–514 (1996).

Montandon F. et al. "Comparison of DNA Reactivity of the Polyphenylethylene Hormonal Agents Diethylsillbestrol, Tamoxifen and Toremifene in Rat and Hamster Liver", Archives of Toxicology (1994) 68: 272–275.

Krieg M et al. "Androgens and Estrogens: Their Interaction With Stroma And Eipthelium Of Human Benign Prostatic Hyperplasia And Normal Prostate", J. Steroid Biochem. vol. 19, No. 1, pp. 155–161, 1983.

* cited by examiner

A.

B.

C.

| TIME AFTER TREATMENT | % CHANGE RELATIVE TO DAY 0 |
|---|---|
| WEEK 3 (n=11) | 9.44 |
| WEEK 4 (n=8) | 115.27 |
| WEEK 5 (n=8) | 271.71 |
| WEEK 6 (n=8) | 600.88 |

| TIME AFTER TREATMENT | % CHANGE RELATIVE TO DAY 0 |
|---|---|
| WEEK 3 (n=12) | −34.58 |
| WEEK 4 (n=8) | −61.01 |
| WEEK 5 (n=8) | −74.51 |
| WEEK 6 (n=6) | −61.72 |

METHOD FOR CHEMOPREVENTION OF PROSTATE CANCER

CROSS REFERENCE TO RELATED APPLICATION

This application is a Continuation-in-Part Application of U.S. Ser. No. 09/531,472, filed Mar. 20, 2000, which is a Continuation-in-Part Application of U.S. Ser. No. 09/436,208, filed Nov. 8, 1999, which is a Continuation-in-Part Application of U.S. Ser. No. 09/306,958, filed may 7, 1999, which claims priority of U.S. Provisional Application No. 60/084,602, filed May 7, 1998, which is hereby icorporated by reference in its entirety.

FIELD OF INVENTION

This invention relates to the chemoprevention of prostate cancer and, more particularly, to a method of preventing prostate carcinogenesis comprising administering to a mammalian subject having a precancerous precursor of prostate adenocarcinoma, a pharmaceutical preparation comprising a chemopreventive agent and analogs and metabolites thereof. The chemopreventive agent prevents, prevents recurrence of, suppresses or inhibit prostate carcinogenesis.

BACKGROUND OF THE INVENTION

Prostate cancer is one of the most frequently occurring cancers among men in the United States, with hundreds of thousands of new cases diagnosed each year. Unfortunately, over sixty percent of newly diagnosed cases of prostate cancer are found to be pathologically advanced, with no cure and a dismal prognosis. One approach to this problem is to find prostate cancer earlier through screening programs and thereby reduce the number of advanced prostate cancer patients, Another strategy, however, is to develop drugs to prevent prostate cancer. One third of all men over 50 years of age have a latent form of prostate cancer that may be activated into the life-threatening clinical prostate cancer form. The frequency of latent prostatic tumors has been shown to increase substantially with each decade of life from the 50s (5.3–14%) to the 90s (40–80%). The number of people with latent prostate cancer is the same across all cultures, ethnic groups, and races, yet the frequency of clinically aggressive cancer is markedly different. This suggests that environmental factors may play a role in activating latent prostate cancer. Thus, the development of chemoprevention strategies against prostate cancer may have the greatest overall impact both medically and economically against prostate cancer.

Because of the high incidence and mortality of prostate cancer, it is imperative to develop chemoprevention strategies against this devastating disease. Understanding those factors that contribute to proste carcinogenesis including the initiation, promotion, and progression of prostate cancer will provide molecular mechanistic clues as to appropriate points of intervention to prevent or halt the carcinogenic process. New innovative approaches are urgently needed at both the basic science and clinical levels to decrease the incidence of prostate cancer as well as to halt or cause the regression of latent prostate cancer. As the frequency of prostate cancer escalates dramatically at the same ages when men are confronted by other competing causes of mortality, simply slowing the progression of prostate adenocarcinoma may be both a more suitable and cost effective health strategy.

Various approaches have been taken to the chemoprevention of prostate cancer. Greenwald, Expanding Horizons in Breast and Prostate Cancer Prevention and Early Detection in J. Cancer Education, 1993, Vol. 8, No. 2, pages 91-I 07, discusses the testing of 5α-reductase inhibitors such as finasteride for the prevention of prostate cancer. Brawley et al., Chemoprevention of Prostate Cancer in Urology, 1994, Vol. 43, No. 5, also mentions 5α-reductase inhibitors as well as difluoromethylomtthine and retinoids as potential chemopreventive agents.

Kelloff et al., Introductory Remarks: Development of Chemopreventive Agents for Prostate Cancer in Journal of Cellular Biochemistry, 1992, Supplement 16H: 1–8, describes National Cancer Institute preclinical studies of seven agents: all-trans-N(4-hydroxyphenyl)retinamide, difluoromethylomfthine, dehydroepiandrosterone, liarozole, lovestatin, oltipraz, and finasteride.

Lucia et al., Chemopreventive Activity of Tamoxifen, N-(4-Hydroxyphenyl)retinamide, and the Vitamin D Analogue Ro24-553 1 for Androgen-promoted Carcinomas of the Rat Seminal Vesicle and Prostate@ in Cancer Research, 1995, Vol. 55, pages 5621–5627, reports chemoprevention of prostate carcinomas in Lobund-Wistar rats by tamoxifen, an estrogen response modifier.

As discussed in Potter et al., A mechanistic hypothesis for DNA adduct formation by tamoxifen following hepatic oxidative metabolism in Carcinogenesis, 1994, Vol, 15, No. 3, pages 439–442, tamoxifen causes liver carcinogenicity in rats, which is attnbuted to the formation of covalent DNA adducts. This reference also reports that the tamoxifen analogue toremifene, which showed a much lower level of hepatic DNA adduct formation than tamoxifen, is non-carcinogenic. Toremifene is an example of a triphenylalkene compound described in U.S. Pat. Nos. 4,696,949 and 5,491,173 to Toivola et al., the disclosures of which are incorporated herein by reference. The parenteral and topical administration to mammalian subjects of formulations containing toremifene are described in U.S. Pat. No. 5,571,534 to Jalonen et al. and in U.S. Pat. No. 5,605,700 to DeGregorio et al., the disclosures of which are incorporated herein by reference.

Toremifene-containing formulations for reversing the multidrug resistance to cancer cells to a cytotoxic drug are described in U.S. Pat. No. 4,990,538 to Harris et al., the disclosure of which is incorporated herein by reference. U.S. Pat. Nos. 5,595,722 and 5,599,844 to Grainger et al., the disclosures of which are incorporated herein by reference, describe methods for identifying agents that increase TGFP levels and for orally administering formulations containing TGFP activators and TGFP production stimulators to prevent or beat conditions characterized by abnormal proliferation of smooth muscle cells, for example, vascular trauma. Disclosed agents for increasing TGFP levels include tamoxifen and its analogue toremifene.

U.S. Pat. Nos. 5,629,007 and 5,636,197 to Audia et al., the disclosures of which are incorporated herein by reference, describe a method of preventing the development of prostatic cancer at risk of developing such cancer, for example, a patient having benign prostatic hyperplasia, by administering to the patient an octahydrobenzo[f]quinolin-3-one compound.

U.S. Pat. No. 5,595,985 to Labrie, the disclosure of which is incorporated herein by reference, also describe a method for treating benign prostatic hyperplasia using a combination of a 5α-reductase inhibitor and a compound that binds and blocks access to androgen receptors. One example of a compound that blocks androgen receptors is flutamide.

U.S. Pat. Nos. 4,329,364 and 4,474,813 to Neri et al., the disclosures of which are incorporated herein by reference, describe pharmaceutical preparations comprising flutamide for delaying and/or preventing the onset of prostate carcinoma. The preparation can be in the form of a capsule, tablet, suppository, or elixdr. Despite these developments, there is a continuing need for agents and methods effective for preventing prostate cancer. The present invention is directed to satisfying this need.

SUMMARY OF THE INVENTION

This invention relates to the chemoprevention of prostate cancer and, more particularly, to a method of preventing prostate carcinogenesis comprising the steps of: administering to a mammalian subject having a precancerous precursor of prostate adenocarcinoma, a pharmaceutical preparation comprising a chemopreventive agent and analogs, and metabolites thereof.

This invention provides a method of administering to a subject an effective dose of an antiestrogen which does not cause the formation of DNA adducts, to prevent, prevent recurrence of, and/or suppress or inhibit prostate carcinogenesis.

This invention provides a method of preventing prostate carcinogenesis comprising the steps of: administering to a subject an effective dose of a chemopreventive agent, toremifene and analogs or metabolites thereof, to prevent, prevent recurrence of, and/or supress or inhibit prostate carcinogenesis.

The present invention is directed to a method of preventing prostate carcinogenesis comprising the steps of: administering to a mammalian subject having a precancerous precursor of prostate adenocarcinoma and does not have prostate cancer, a pharmaceutical preparation comprising a chemopreventive agent having the formula:

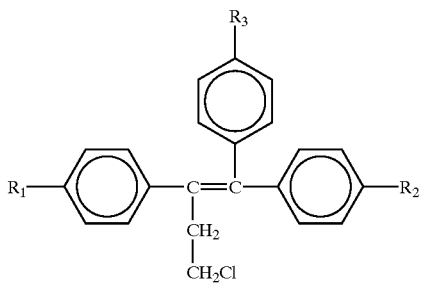

(1)

wherein $R_1$ and $R_2$, which an be the same or different, are H or OH, $R_3$ is $OCH_2CH_2NR_4R_5$, wherein $R_4$ and $R_5$, which can be the same or different, are H or an alkyl group of 1 to about 4 carbon atoms and analogs, and metabolites thereof; and their pharmaceutically acceptable carrier, diluents, salts, esters, or N-oxides, and mixtures thereof. In one embodiment the precancerous precursor of prostate adenocarcinoma is prostate intraepithelial neoplasia (PIN). In one embodiment the precancerous precursor of prostate adenocarcinoma is high grade prostate intraepithelial neoplasia (PIN).

The present invention provides a safe and effective method for preventing prostate carcinogenesis, suppressing or inhibiting latent prostate cancer and is particularly useful for treating subjects having an elevated risk of developing prostate cancer, for example, those having benign prostatic hyperplasia, prostate intraepithelial neoplasia (PIN), or an abnormally high level of circulating prostate specific antibody (PSA), or who have a family history of prostate cancer.

DETAILED DESCRIPTION OF THE INVENTION

Figure 1:
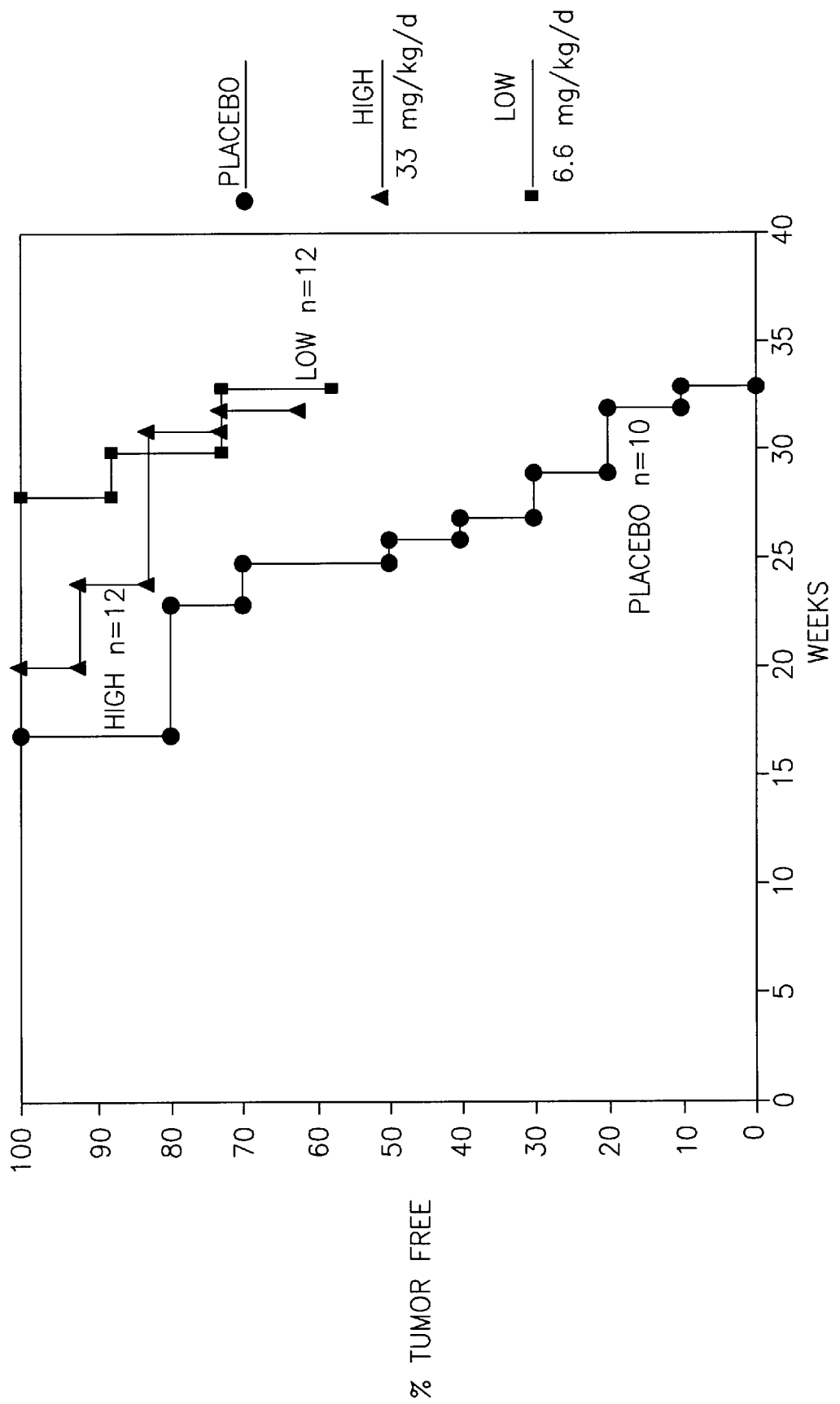
FIG. 1: A graph illustrating the chemopreventtve effects of toremifene in the TRAMP model.

This invention provides a method for preventing prostate carcinogenesis; 2) methods for suppressing or inhibiting prostate cancer, 3) methods for reducing the risk of developing prostate cancer; and 4) methods for increasing the survival rate of a subject using an antiestrogen which does not cause the formation of DNA adducts as the prostate chemopreventive. In one embodiment the antiestrogen which does not cause the formation of DNA adducts is a chemopreventive agent having the formula:

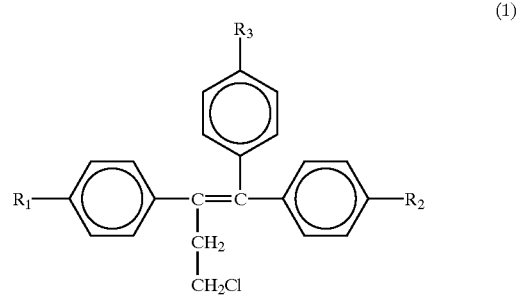

(1)

wherein $R_1$ and $R_2$i which can be the same or different, are H or OH, $R_3$ is $OCH_2CH_2NR_4R_5$, wherein $R_4$ and $R_5$, which can be the same or different, are H or an alkyl group of 1 to about 4 carbon atoms and analogs and metabolites thereof; and their pharmaceutically acceptable carrier, diluents, salts, esters, or N-oxides, and mixtures thereof. A composition and/or a pharamceutical composition may comprise the chemopreventive agent.

As demonstrated herein, toremifene is one example of an antiestrogen which does not cause the formation of DNA adducts which is a prostate chemopreventive agent In the experiments conducted herein in both animal and human studies the antiestrogen, was shown to prevent prostate cancer. The prostates were actually dissected and evaluated both histologically and by wholemount analysis. Also, toremifene was tested for the prevention of prostate cancer by treating LNCaP xenografts in nude mice. As is shown, the data is quite dramatic, not only has an antiestrogen such as toremifine inhibited growth, but actually toremifene was able to produce regression of the tumors. Further, in human studies conducted with the antiestrogen, high grade PIN (HGPIN) which has been established and time tested as a precursor lesion for human prostate cancer also known as latent prostate cancer, has shown regression. Thus, demonstrating that the antiestrogen toremifene is a prostate chemropreventive agent.

The present invention is directed to a method for preventing prostate carcinogenesis. Antiestrogens which act as prostate chemopreventive agents include but are not limited to: toremffene and analogs or synthetics thereof; selective estogen receptor modulators (SERMS), triphenylethylenes which include droloxifen, idoxifene, (2)-4-OH-tamoxifene; arzoxifene; chromans such as levomeloxifene, and centchroman; benzothiophenes such as ramoxfene, and LY 353381; naphthalens such as CP336,156; phytoestrogens such as isoflavanoids including daidzein, genistein, yenoestrogens; coumestrol: zearalenone; daidzein; apigenin; waempferol; phioretin; biochanin A; naringenin; formononetin; iprifla-vone; quercetin; chrysin; flavonoids; flavones, isoflavones, flavanones, and chalcones); coumestans; mycoestrogens; resorcydic acid factone: nafoxideneand equol, and lignan including enterodiol and enterolactone; and other compounds which are known in the art as follows: ICI 164,384, ICI 182, 780; TAT-59, EM-652 (SCG 57068), EM-800 (SCH57050), EM-139, EM-651, EM-776, and peptide antagonist of human estrogen receptors.

This invention involves administering to a subject a pharmaceutical preparation of a chemopreventive agent having the formula:

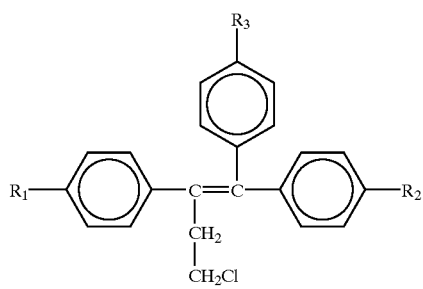

(1)

wherein $R_1$ and $R_2$, which can be the same or different, are H or OH, $R_3$ is $OCH_2CH_2NR_4R_5$, wherein $R_4$ and $R_5$, which can be the same or different, are H or an alkyl group of 1 to about 4 carbon atoms and analogs, and metabolites thereof, and their pharmaceutically acceptable carrier, diluents, salts, esters, or N-oxides, and mixtures thereof.

This invention provides the use of a pharmaceutical composition for preventing prostate cancer, the recurrence of, suppression or inhibition of prostate carcinogenesis, or increasing the survival rate of a subject having prostate cancer, comprising an antiestrogen which does not cause the formaton of DNA adducts and a suitable diluent. The antiestrogens include the antiestrogens provided above.

This invention provides for the use of a pharmaceutical composition for preventing prostate cancer, the recurrence of, suppression or inhibition of prostate carcinogenesis, or increasing the survival rate of a subject having prostate cancer, comprising a chemopreventive agent having the formula:

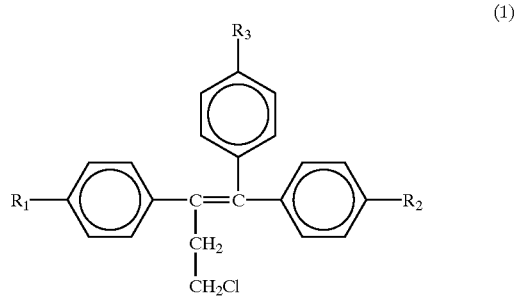

(1)

wherein $R_1$ and $R_2$, which can be the same or different, are H or OH, $R_3$ is $OCH_2CH_2NR_4R_5$, wherein $R_4$ and $R_5$, which can be the same or different, are H or an alkyl group of 1 to about 4 carbon atoms; and their pharmaceutically acceptable carrier, diluents, salts, esters, or Noxides, and mixtures thereof.

The present invention provides a safe and effective method for preventing carcinogenesis, suppressing or inhibiting latent prostate cancer and is particularly useful for treating subjects having an elevated risk of developing prostate cancer, for example, those having benign prostatc hyperplasia, prostate intraepithejial neoplasia (PIN), or an abnormally high level of circulating prostate specific antibody (PSA), or who have a family history of prostate cancer. In one embodiment the subject is a mammalian subject. In another embodiment the subject is a human subject.

The compound 4-chloro-1,2-diphenyl-1-[4-[2-(N,N-dimethylamino) ethoxy]phenyl]-1-butene of formula (I), where $R_1$ and $R_2$ are each H and $R_4$ and $R_5$ are each methyl, is named toremifene. Toremifene has been shown safe and effective as an anti-tumor compound. On administration, toremifene has several metabolites that are also biologically active.

This invention also provides for use of an antiestrogen which does not form DNA adducts and toremifene and analogs or metabolites thereof, which are well known to those skilled in the art. Other examples of chemopreventive agents of formula (I) are the following: 4-chloro-1,2-diphenyl-1-[4-[2-(N-methylamino)ethoxy]phenyl]-1-butene; 4-chloro-1,2-diphenyl-1-[4-[2-(N,N-diethylamino)ethoxy]phenyl]-1-butene; 4-chloro-1,2-diphenyl-1-[4-(aminoethoxy)phenyl]-1-butene; 4chloro-1-(4-hydroxyphenyl)-1-[4-2-(N,N-dimethylamino)ethoxy]pheny]-2-phenyl-1-butene; 4-chloro-1-(4-hydroxyphenyl)-1-[4-[2-(N-methylamino)ethoxy]phenyl]-2-phenyl-1-butene; and 4-chloro-1,2-bis(4-hydroxyphenyl)-1-[4-[2-(N,N-dimethylamino)ethoxy]phenyl]-1-butene.

The invention encompasses pure (Z)- and (E)-isomers of the compounds and mixtures thereof as well as pure (RR, SS)- and (RS,SR)-enantiomer couples and mixtures thereof.

The agent compounds of formula (I) can be prepared according to procedures described in the previously cited U.S. Pat. Nos. 4,696,949 and 5,491,173 to Toivola et al.

The invention includes pharmaceutically acceptable salts of amino-substituted compounds with organic and inorganic acids, for example, citric acid and hydrochloric acid. The invention also includes N-xoides of the amino substituents of the compounds of formula (I). Pharmaceutically acceptable salts can also be prepared from the phenolic compounds by treatment with inorganic bases, for example, sodium hydroxide. Also, esters of the phenolic compounds can be made with aliphatic and aromatic carboxylic acids, for example, acetic acid and benzoic acid esters.

As used herein, Apharmaceutical composition@ means therapeutically effective amounts of the agent together with suitable diluents, preservatives, solubilizers, emulsifiers, adjuvant and/or carriers. A "therapeutically effective amount" as used herein refers to that amount which provides a therapeutic effect for a given condition and administration regimen. Such compositions are liquids or lyophilized or otherwise dried formulations and include diluents of various buffer content (e.g., Tris-HCl., acetate, phosphate), pH and ionic strength, additives such as albumin or gelatin to prevent absorption to surfaces, detergents (e.g., Tween 20, Tween 80, Pluronic F68, bile acid salts). solubilizing agents (e.g., glycerol, polyethylene glycerol), anti-oxidants (e.g., ascorbic acid, sodium metabisulfite), preservatives (e.g., Thimerosal, benzyl alcohol, parabens), bulking substances or tonicity modifiers (e.g., lactose, mannitol), covalent attachment of polymers such as polyethylene glycol to the protein, complexation with metal ions, or incorporation of the material into or onto particulate preparations of polymeric compounds such as polylactic acid, polglycolic acid, hydrogels, etc, or onto liposomes, microemulsions, micelles, unilamellar or multilamellar vesicles, erythrocyte ghosts, or spheroplasts. Such compositions will influence the physical state, solubility, stability, rate of in vivo release, and rate of in vivo clearance. Controlled or sustained release compositions include formulation in lipophilic depots (e.g., fatty acids, waxes, oils). Also comprehended by the invention are particulate compositions coated with polymers (e.g., poloxamers or poloxamines). Other embodiments of the compositions of the invention incorporate particulate forms protective coatings, protease inhibitors or permeation enhancers for various routes of administration, including parenteral, pulmonary, nasal and oral. In one embodiment the pharmaceutical composition is administered parenterally, paracancerally, transmucosally, transdermally, intramuscularly, intravenously, intradermnally, subcutaneously, intraperitonealy, intraventrcularly, intracranially and intratumorally. The dosage may be in the range of 20–80 mg/day. In another embodiment the dosage is in the range of 35–46 mg/day. In another embodiment the dosage is in the range of 40–60 mg/day. In another embodiment the dosage is in a range of 45–60 mg/day. The dosage may be 40–45 mg/day. The dosage may be 60 mg/day. The dosage may be 45 mg/day.

Further, as used herein pharmaceutically acceptable carrier are well known to those skilled in the art and include, but are not limited to, 0.01–0.1M and preferably 0.05M phosphate buffer or 0.8% saline. Additionally, such pharmaceutically acceptable carriers may be aqueous or nonqueous solutions, suspensions, and emulsions. Examples of non-aqueous solvents are propylene glycol, polyethylene glycol, vegetable oils such as olive oil, and injectable organic esters such as ethyl oleate. Aqueous carriers include water, alcoholic/aqueous solutions, emulsions or suspensions, including saline and buffered media. Parenteral vehicles include sodium chloride solution, Ringer's dextrose, dextrose and sodium chloride, lactated Ringers or fixed oils. Intravenous vehicles include fluid and nutrient replenishers, electrolyte replenishers such as those based on Ringer's dextrose, and the like. Preservatives and other additives may also be present, such as, for example, antimicrobials, antioxidants, collating agents, inert gases and the like.

The term "adjuvant" refers to a compound or mixture that enhances the immune response to an antigen. An adjuvant can serve as a tissue depot that slowly releases the antigen and also as a lymphoid system activator that non-specifically enhances the immune response (Hood et al., *Immunology, Second Ed.*, 1984, Benjamin/Cummings: Menlo Park, Calif., p. 384). Often, a primary challenge with an antigen alone, in the absence of an adjuvant, will fail to elicit a humoral or cellular immune response. Adjuvant include, but are not limited to, complete Freund's adjuvant, incomplete Freund's adjuvant, saponin, mineral gels such as aluminum hydroxide, surface active substances such as lysolecithin, pluronic polyols, polyanions, peptides, oil or hydrocarbon emulsions, keyhole limpet hemocyanins, dinitrophenol, and potentially useful human adjuvant such as BCG (bacille Calmette-Guerin) and *Corynebactenium parvum*. Preferably, the adjuvant is pharmaceutically acceptable.

Controlled or sustained release compositions includ formulation in lipophilic depots (e.g. fatty acids, waxes, oils). Also comprehended by the invention are particulate compositions coated with polymers (e.g. poloxamers or poloxamines) and the compound coupled to antibodies directed against tissue-specific receptors, ligands or antigens or coupled to ligands of tissue-specific receptors. Other embodiments of the compositions of the invention incorporate particulate forms protective coatings, protease inhibitors or permeation enhancers for various routes of administration, including parenteral, pulmonary, nasal and oral. Compounds modified by the covalent attachment of water-soluble polymers such as polyethylene glycol, copolymers of polyethylene glycol and polypropylene glycol, carboxymethyl cellulose, dextran, polyvinyl alcohol, polyynylpyrrolidone or polyproline are known to exhibit substantially longer half-lives in blood following intravenous injection than do the corresponding unmodified compounds (Abuchowski et al., 1981; Newmark et al., 1982; and Katre et al., 1987). Such modifications may also increase the compound's solubility in aqueous solution. eliminate aggregation, enhance the physical and chemical stability of the compound, and greatiy reduce the immunogenicty and reactivity of the compound. As a result, the desired in vivo biological activity may be achieved by the administration of such polymer-compound abducts less frequently or in lower doses than with the unmodified compound.

In yet another embodiment, the pharmaceutical composition can be delivered in a controlled release system. For example, the agent may be administered using intravenous infusion, an implantable osmotic pump, a transdermal patch, liposomes, or other modes of administration. In one embodiment, a pump may be used (see Langer, supra; Sefton, CRC Crit. Ref. Biomed. Eng. 14:201 (1987); Buchwald et al., Surgery 88:507 (1980); Saudek et al., N. Engl. J. Med. 321:574 (1989). In another embodiment, polymeric materials can be used. In yet another embodiment, a controlled release system can be placed in proximity of the therapeutic target, i.e., the brain, thus requiring only a fraction of the systemic dose (see, e.g., Goodson, in Medical Applications of Controlled Release, supra, vol. 2, pp. 115–138 (1984). Preferably, a controlled release device is introduced into a subject in proximity of the site of inappropriate immune activation or a tumor. Other controlled release systems are discussed in the review by Langer (Science 249:1527–1533 (1990).

The method of the present invention for preventing prostate carcinogenesis involves administering to a mammalian subject a pharmaceutical preparation comprising chemopreventive agent or a metabolite or salt thereof. The pharmaceutical preparation can comprise the chemopreventive agent alone, or can further include a pharmaceutically acceptable carrier, and can be in solid or liquid form such as tablets, powders, capsules, pellets, solutions, suspensions, elixirs, emulsions, gels, creams, or suppositories, including rectal and urethral suppositories. Pharmaceutically acceptable carriers include gums, starches, sugars, cellulosic materials, and mixtures thereof. The pharmaceutical preparation containing the chemopreventive agent can be administered to a subject by, for example, subcutaneous implantation of a pellet; in a further embodiment, the pellet provides for controlled release of chemopreventive agent over a period of time. The preparation can also be administered by intravenous, intraarterial, or intramuscular injection of a liquid preparation, oral administration of a liquid or solid preparation, or by topical application. Administration can also be accomplished by use of a rectal suppository or a urethral suppository. The pharmaceutical preparation can also be a parenteral formulation; in one embodiment, the formulation comprises a liposome that includes a complex of a chemopreventive agent such as, for example, toremifene and a cyclodextrin compound, as described in the previously cited U.S. Pat. No. 5,571,534 to Jalonen et al.

The pharmaceutical preparations of the invention can be prepared by known dissolving, mixing, granulating, or tablet-forming processes. For oral administration, the chemopreventive agents or their physiologically tolerated derivatives such as salts, esters, N-oxides, and the like are mixed with additives customary for this purpose, such as vehicles, stabilizers, or inert diluents, and converted by customary methods into a suitable form for administration, such as tablets, coated tablets, hard or soft gelatin caps aqueous, alcoholic or oily solutions. Examples of suitable inert vehicles are conventional tablet bases such as lactose, sucrose, or cornstarch in combination with binders like acacia, cornstarch, gelatin, or with disintegrating agents such as cornstarch, potato starch, alginic acid, or with a lubricant like stearic acid or magnesium stearate. Examples of suitable oily vehicles or solvents are vegetable or animal oils such as sunflower oil or fish-liver oil. Preparations can be effected both as dry and as wet granules. For parenteral administration (subcutaneous, intravenous, intraarterial, or intramuscular injection), the chemopreventive agents or their physiologically tolerated derivatives such as salts, esters, N-oxides, and the like are converted into a solution, suspension, or emulsion, if desired with the substances customary and suitable for this purpose, for example, solubilizers or other auxiliaries. Examples are: sterile liquids such as water and oils, with or without the addition of a surfactant and other pharmaceutically acceptable adjuvants. Illustrative oils are those of petroleum, animal, vegetable, or synthetic origin, for example, peanut oil, soybean oil, or mineral oil. In general, water, saline, aqueous dextrose and related sugar solutions, and glycols such as propylene glycols or polyethylene glycol are preferred liquid carriers, particularly for injectable solutions.

The preparation of pharmaceutical compositions which contain an active component is well understood in the art. Typically, such compositions are prepared as an aerosol of the polypeptide delivered to the nasopharynx or as injectables, either as liquid solutions or suspensions, however, solid forms suitable for solution in, or suspension in, liquid prior to injection can also be prepared. The preparation can also be emulsified. The active therapeutic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the composition can contain minor amounts of auxiliary substances such as wetting or emulsifying agents, pH buffering agents which enhance the effectiveness of the active ingredient.

An active component can be formulated into the composition as neutralized pharmaceutically acceptable salt forms. Pharmaceutically acceptable salts include the acid addition salts (formed with the free amino groups of the polypeptide or antibody molecule) and which are formed with inorganic acids such as, for example, hydrochloric or phosphoric acids, or such organic acids as acetic, oxalic, tartaric, mandelic, and the like. Salts formed from the free carboxyl groups can also be derived from inorganic bases such as, for example, sodium, potassium, ammonium, calcium, or ferric hydroxides, and such organic bases as isopropylamine, trimethylamine, 2-ethylamino ethanol, hisfidine, procaine, and the like.

For topical administration to body surfaces using, for example, creams, gels, drops, and the like, the chemopreventive agents or their physiologically tolerated derivatives such as salts, esters, N-oxides, and the like are prepared and applied as solutions, suspensions, or emulsions in a physiologically acceptable diluent with or without a pharmaceutical carrier.

In another embodiment, the active compound can be delivered in a vesicle, in particular a liposome (see Langer, Science 249:1527–1533 (1990); Treat et al., in *Liposomes in the Therapy of Infectious Disease and Cancer*, Lopez-Berestein and Fidler (eds.), Liss, New York, pp. 353–365 (1989); Lopez-Berestein, ibid., pp. 317–327; see generally ibid).

The pharmaceutical compositions of the present invention are particularly useful for treating a subject having an elevated risk of developing prostate cancer. High-risk subjects include, for example, those having benign prostatic hyperplasia, prostatic intraepithelial neoplasia (PIN), or an abnormally high level of circulating prostate specific antibody (PSA), or who have a family history of prostate cancer.

Further, the prostate chemopreventive agent may be administered in combination with other cytokines or growth factors include but are not limited to: IFNγ or α, IFN-β; interleukin (IL) 1, IL-2, IL-4, IL-6 IL-7, IL-12, tumor necrosis factor (TNF) α, TNF-β, granulocyte colony stimulating factor (G-CSF), granulocyte/macrophage CSF (GM-CSF); accessory molecules, including members of the integrin superfamily and members of the Ig superfamily such as, but not limited to, LFA-1, LFA-3, CD22, and B7-1, B7-2, and ICAM-1 T cell costimulatory molecules.

The chemopreventive agent may precede or follow a DNA damaging agent treatment by intervals ranging from minutes to weeks. Protocols and methods are known to those skilled in the art. DNA damaging agents or factors are known to those skilled in the art and means any chemical compound or treatment method that induces DNA damage when applied to a cell. Such agents and factors include radiation and waves that induce DNA damage such as, gamma irradiation. X-rays, UV-irradiation, microwaves, electronic emissions, and the like. A variety of chemical compounds, also described as "chemotherapeutic agents", function to induce DNA damage, all of which are intended to be of use in the combined treatment methods disclosed herein. Chemotherapeutic agents contemplated to be of use, include, e.g., adriamycin, 5-fluorouracil (5FU), etoposide (VP-16), camptothecin, actinomycin-D, mitomycin C, cisplatin (CDDP) and even hydrogen peroxide. The invention also encompasses the use of a combination of one or more DNA damaging agents, whether radiation-based or actual compounds, such as the use of X-rays with cisplatin or the use of cisplatin with etoposide.

In another embodiment one may irradiate the localized tumor site vith DNA damaing radiation such as X-rays, UV-light, gamma-rays or even microwaves. Alternatively, the tumor cells may be contacted with the DNA damaging agent by administering to the subject a therapeutically effective amount of a pharmaceutical composition comprising a DNA damaging compound such as, adriamycin, 5-fluorouracil, etoposide, camptothecin, actinomycin-D, mitomycin C, or more preferably, cisplatin. Agents that damage DNA also include compounds that interfere with DNA replication, mitosis and chromosomal segregation. Such chemotherapeutic compounds include adriamycin, also known as doxorubicin, etoposide, verapamil, podophyllotoxin, and the like.

Other factors that cause DNA damage and have been used extensively include what are commonly known as gamma-rays, X-rays, and/or the directed delivery of radioisotopes to tumor cells. Other forms of DNA damaging factors are also contemplated such as microwaves and UV-irradiation. It is most likely that all of these factors effect a broad range of damage DNA, on the precursors of DNA, the replication and repair of DNA, and the assembly and maintenance of chromosomes.

As can be readily appreciated by one of ordinary skill in the art, the methods and pharmaceutical compositions of the present invention are particularly suited to administration to a mammal, preferable a human subject.

Intermediate endpoint biomarkers are measurable biologic alterations in tissue that occur between the initiation of and the development of frank neoplasia. A biomarker is validated if the final endpoint, cancer incidence, were also reduced by the putative chemopreventive agent. Intermediate biomarkers in cancer may be classified into the following gmups: histologic, proliferation, differentiation and biochemical markers. In any chemoprevention strategy, the availability of histologically recognizable and accepted pre-cancerous lesions constitutes an important starting point For the prostate, a histological marker is a precancerous precursor of prostatic adenocarcinoma of which prostatic intraepithelial neoplasia (PIN) is an example of. PIN appears as an abnormal proliferation within the prostatic ducts of premalignant foci of cellular dysplasia and carcinoma in situ without stromal invasion PIN and histological prostate cancer are morphometrically and phenotypically similar. Thus, the development of high grade PIN represents an important step in the progression pathway whereby the normal prostate develops PIN, histological prostate cancer, invasive clinical prostate cancer, and metastases.

The following examples are presented in order to more fully illustrate the preferred embodiments of the invention. They should in no way be construed, however, as limiting the broad scope of the invention.

EXPERIMENTAL DETAILS SECTION

EXAMPLE I

Transgenic Adenocarcinoma Mouse Prostate

The study of prostate cancer chemoprevention has been hindered by the lack of appropriate animal models. The recent development of the transgenic adenocarcinoma mouse prostate (TRAMP) model enables the study of chemoprevention. In the TRAMP model, which is described in Greenberg et al., AProstate cancer in a transgenic mouse,@ Proc. Natl Acad. Sci. USA, 1995, Vol. 92, pages 3439–3443, the PB-SV40 large T antigen (PB-Tag) transgene is expressed specifically in the epithelial cells of the murine prostate. As a result, this model has several advantages over currently existing models: 1) mice develop progressive forms of prostatic epithelial hyperplasia as early as 10 weeks and invasive adenocarcinoma around 18 weeks of age; 2) the metastatic spread of prostate cancer pattern mimics human prostate cancer with the common sites of metastases being lymph node, lung, kidney, adrenal gland, and bone; 3) the development as well as the progression of prostate cancer can be followed within a relatively short period of 10–30 weeks; 4), the tumors arise with 100% frequency; and 5) the animals may be screened for the presence of the prostate cancer transgene prior to the onset of clinical prostate cancer to directly test treatment with chemopreventive agents that may alter prostate carcinogenesis.

The TRAMP transgenic mouse model is an excellent in vivo model to determine the mechanisms of initiation and promotion of prostate cancer and to test the effectiveness of potential chemopreventive agents. These mice progressively develop prostate epithelial hyperplasia, PIN, and then prostate cancer within a short period of 17 weeks).

Chemopreventive treatment of hybrid TRAMP mice is initiated 30 days postnatally, using chemopreventive agents at a level of about 0.5–50 mg/kg of subject weight/day, preferably about 6–30 mg/kg of subject weight/day. The chemopreventive agents are conveniently processed into 21-day and 90-day pellets (prepared by Innovative Research of America, Sarasota, Fla.) and delivered as subcutaneous implants. Control animals receive placebo implants. In each drug treatment group, animals are sacrificed at 5,7, 10, 15,20,25,30,40, and 50 weeks of age until the development of a palpable tumor. Blood is collected and pooled per treatment time point to evaluate changes in serum testosterone and estradiol. Prostatic tissues are harvested for morphometric, histologic, and molecular studies.

Figure 2:
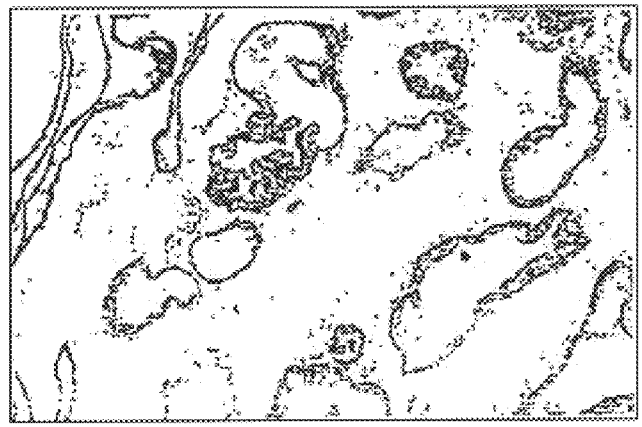
FIGS. 2A–2C: H&E sections illustrating ventral prostate cells in normal mice and prostate carcinoma in TRAMP mice included in the study.
Figure 2:
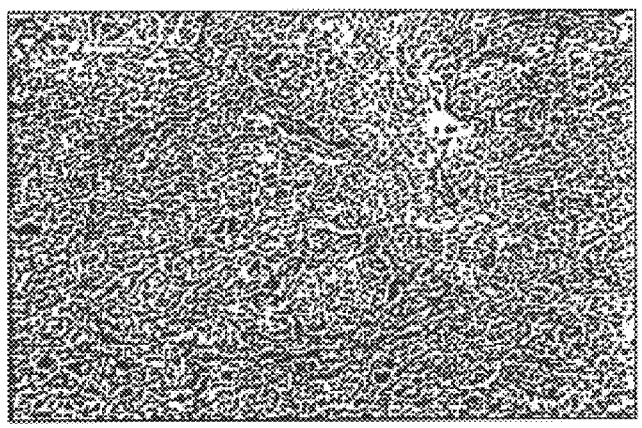
Figure 2:
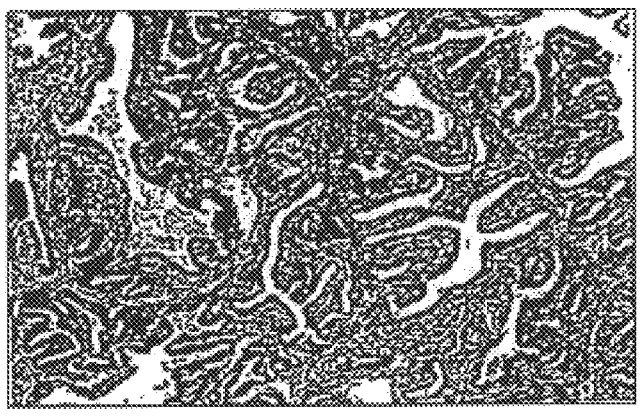

The following test procedures are employed:

1) Prostate wholemount analysis is serially performed to detect changes in prostate ductal morphology over time with and without treatment; examples are shown in FIG. 2. Tissue sections are evaluated histologically by H&E and Masson-trichome standard staining. The emergence of PIN is assessed and graded (I-mild to III-severe).

2) Serum estradiol and total testosterone levels are measured (RIA) for each age interval to assess any changes in these hormones as a result of chemopreventive agents.

EXAMPLE 2

Immunohistochemistry Data Analysis

Microscopy images of each tissue section are evaluated by using computer-assisted (Mac 9500-1 32 computer and monitor) image quantitation (NIH-Image 1.6 PPC) using Kodak DCS 460 camera on Nikon Microphot-FX microscope and quantitated by using a color-assisted quantitative system image analysis (IPLab Spectrum 3.1, Scanalytics, Inc., Va.) that discriminates color differences of stained tissue sections. Thresholds are set to identify various tissue components of the prostate. The area pixer densities corresponding to each of these tissue components are calculated for each full screen of the color monitor. A total of 5 screens per prostate section are averaged. Immunohistochemical images can be digitalized and quantitated to enable statistical evaluation by determination of sample correlation coefficients and probability (2-tailed).

EXAMPLE 3

Study of Chemoproventlve Activity

A study was undertaken to test the efficacy of chemopreventive agents in TRAMP transgenic animals (PBTag X FVBwt)(provided by Dr. Norman Greenberg, Baylor College of Medicine, Tex.). These mice showed preliminary signs of cancer as early as 10 weeks. The TRAMP transgenic male litters were screened for the Large T ag transgene, and the positive males were used in the study. The antiestrogen toremifene, which was to be tested for its possible chemopreventive effects, was incorporated in customized pellets (Innovative Research of America, Sarasota, Fla.), and chemopreventive treatment of mice was initiated postnatally at 30 days (average mouse weight 14 g). Four groups of 10–12 animals each received subcutaneous implantations of 90 day-release toremifene-containing pellets. The diffusible drug dosage, adjusted for growth related changes in weight, was designed to deliver either a low dose (6 mg/kg) or a high dose (30 mg/kg) of toremifene. Control animals (n=10) received placebo implants. The efficacy of the treatment was measured by the absence of palpable tumor forrnation. The murine prostate tumors were harvested and evaluated by molecular and histological techniques.

Using the TRAMP transgenic model of prostate cancer, in which every animal that inherits the prostate cancer gene develops prostate cancer, it was demonstrated that toremifene both increases the latency and decreases the incidence of prostate cancer.

As shown in FIG. 1 the effects of low and high dose toremifene were both effective. The formation in the TRAMP mouse ventral prostate was noted at week 17 for the placebo group (n=10), at week 19 for the high dose toremrifene-treated group(n=12), and at week 28 for the low dose toremifene-treated group (n=12). Thus, 5 treatment by toremifene substantially increased the latency period by up to 11 weeks for the development of cancer in the ventral prostate of TRAMP mice.

Since the toremifene-treated animals did not reach the 50% tumor development point during the perlod of the study, the time in which 25% of the animals had tumors was compared among groups. Tumors were palpable in 25% of 10 the animals by week 23 in the placebo group and by 30–31 weeks in the high and low toremifene groups, a delay of 7–8 weeks. Both low toremifene and high toremifene vs placebo were significant by log rank and Wilcoxon statistical analysis, as shown in Table 1 below.

TABLE 1

Statistical Analysis

|  | Log-Rank P | Wilcoxon p |
|---|---|---|
| Low toremifene vs placebo | 0.0003* | 0.0004* |
| High toremifene vs placebo | 0.0017* | 0.0071* |

*significance P < 0.05

At week 33, a point when all of the control animals had developed tumors, 72% of the low dose and 60% of the high dose toremifene-freated animals were still tumor-free. Thus, toremifene treatment at both low and high dosages resulted in a greatly decreased incidence of tumors in the ventral prostate of TRAMP mice.

These results, obtained in accordance with the present invention, would not have been predicted from those reported in the aforementioned paper of Lucia et al., which describes the administering at two dosage levels of tamoxifen, a close structural analog of toremifene, to Lobund-Wistar rats having prostate carcinomas induced by treatment with a combination of an initiator and a promoter. In the Lucia et al. reference, it is reported that only 22–26% of the animals receiving the lower dose and only 32–50% of those receiving the higher dose of tamoxifen remained free of tumors in the anterior prostate. It should be noted that the anterior prostate of a rodent, unlike its ventral prostate, has no corresponding segment in the prostate of a human subject.

In Lucia et al., it is further stated that the initiator-promoter combination employed in the described procedures, although effective in inducing cancer in the anterior prostate of the test animals, failed to induce carcinomas in the ventral prostate. Therefore there is no basis to expect a chemopreventive effect on tumors in the ventral prostate by administering tamoxifen to Lobund-Wistar rats or to humans.

As already discussed, administering toremifene produces a substantial chemopreventive effect against tumors in the ventral prostate of TRAMP mice. This result is encouraging for a similar beneficial effect on human subjects, whose prostate does include a segment corresponding to the ventral prostate of rodents.

EXAMPLE 4

Histological Examination of Prostate Tissue

Tumors from the placebo and high toremifene treated groups taken at the time of palpation were evaluated histologically. FIG. 2A is an H&E section of the ventral prostate of a 17-week-old normal adult mousb. FIG. 2B, a section of the ventral prostate of a placebo-treated 16-week-old TRAMP mouse, shows that, unlike the normal prostate structure depicted in FIG. 2A, the TRAMP mouse ventral prostate is characterized by sheets of undifferentiated, anaplastc cells with a high mitotic index. In contrast, as shown in FIG. 2C, the prostate of a toremifene-treated 30week-old TRAMP mouse retains much of the normal glandular architecture and ha tumors with a more differentiated structure, the mitotic index being much lower than that for the placebo-treated animal. These results indicate that toremifene, even at low dosage, is able to suppress prostate carcinogenesis in the TRAMP model.

EXAMPLE 5

Use of Chemopreventive Efficacy of Toremifene Against Prostate Cancer in the TRAMP Mouse Model This experiment confirms and demonstrates the chemopreventive efficacy of toremifene. This present study focuses on the histological and molecular changes associated with development of prostate tumor in control animals and the mechanism of toremifene chemopreventive action with TRAMP animals which are bred, screened and treated with sustained-release drug pellets. At predetermined times, groups of 5 animals were sacrificed and their prostates were removed for analysis. The prostate glands were evaluated for the presence of tumor by histology, wholemount dissections, and large T antigen immunohistochemistry. To date, the Placebo and the Toremifene treatments have been completed for the 7, 10, 15 and 20 week time-points and the results are described below.

Figure 3:
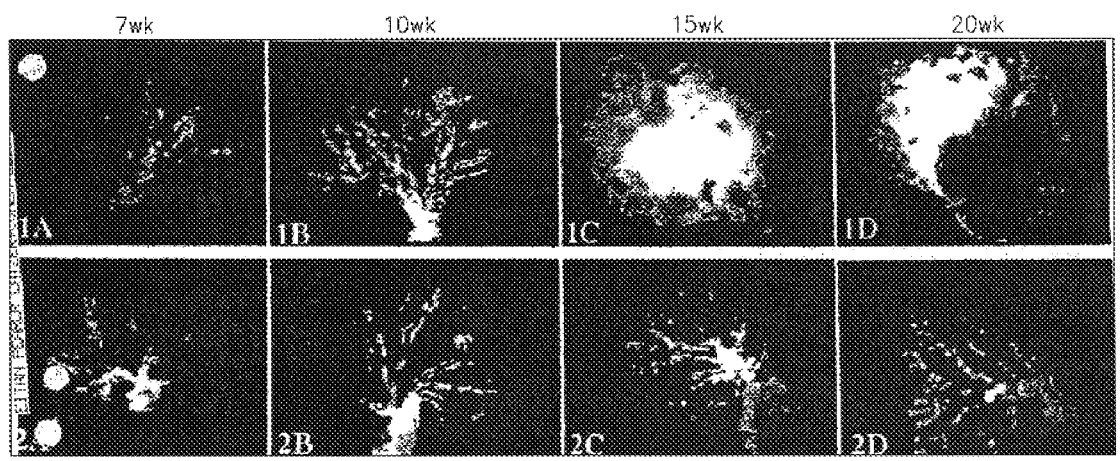
FIG. 3: Effect of Toremifene on ventral prostate development in the TRAMP mouse.
Figure 4:
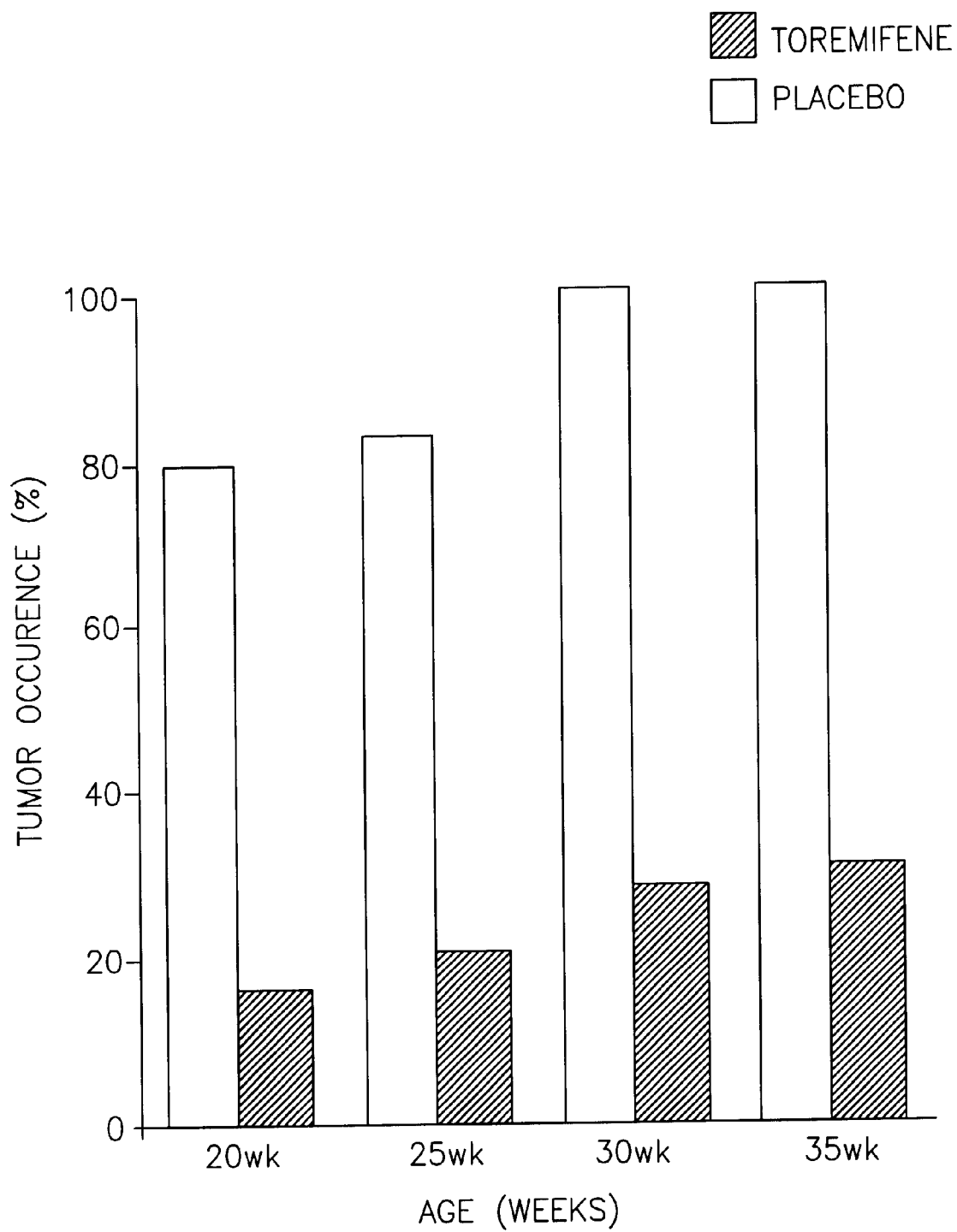
FIG. 4: Effect of Toremifene on tumor occurrence in the TRAMP mice.
Figure 5:
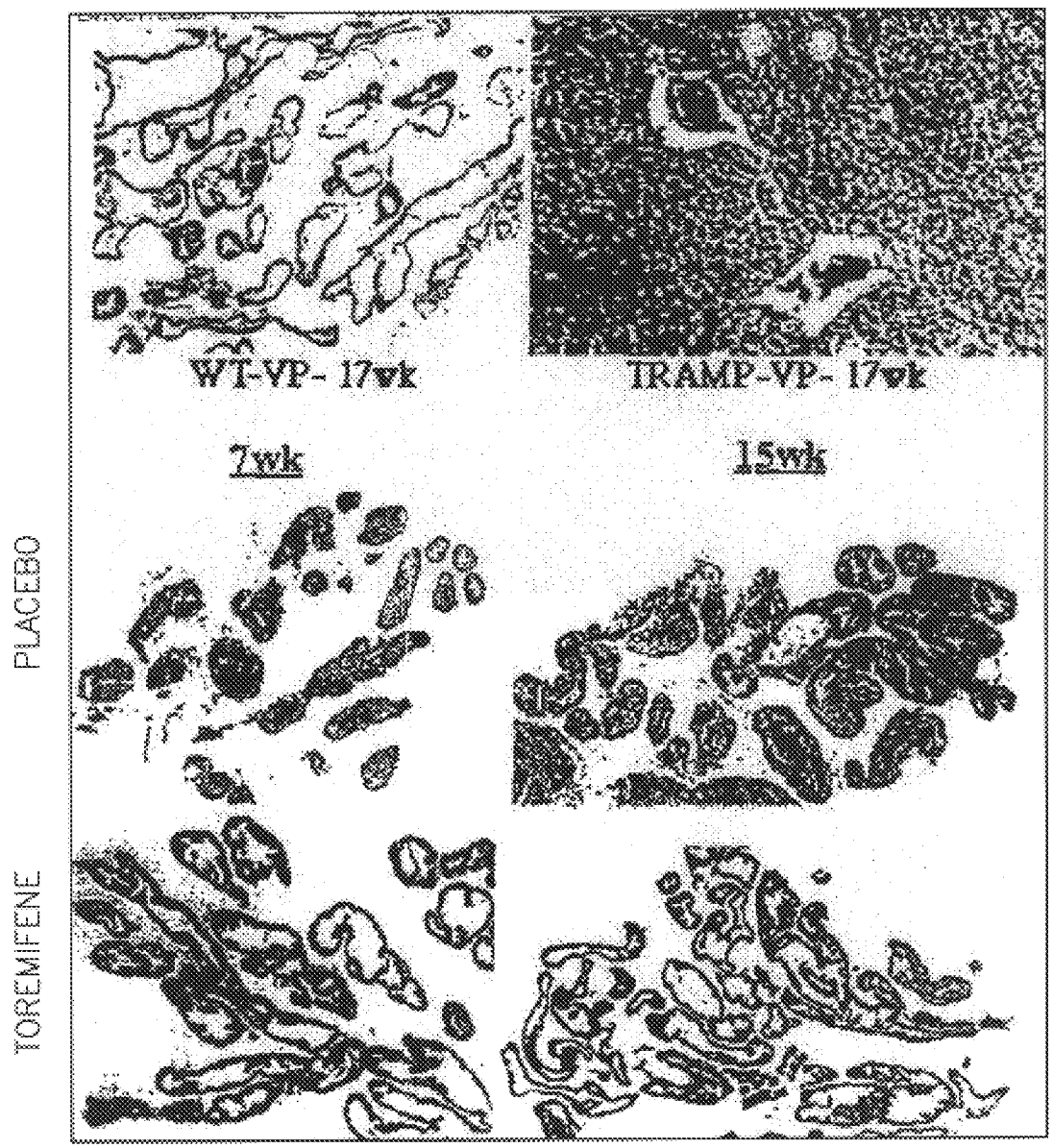
FIG 5: Effect of Toremifene on tumor development in the TRAMP model.

Results: Prostatic wholemounts for 7,10,15, and 20 weeks for the various groups have been completed. Wholemount analysis revealed that placebo treated mice developed prostate tumors by 15–20 weeks of age similar to the previous pilot study. Moreover, the Toremtfene treated animals had a delay in the occurrence of prostate cancer up to 20 weeks (FIG. 3). By 20 weeks, there is a striking delay in tumor occurrence in the Toremifene treated group up to 35 weeks FIG. 4). These data confirm that even with a more sensitive assessment of tumorigenicity, Toremifene exhibited chemopreventive activity. For histological evaluation, tissue samples were fixed, processed and paraffin embedded. Sections (5 pM thick) were cut and stained by routine H&E method. Toremifene inhibited the ductal development and tissue differentiation (compare the 17 weeks TRAMP mouse prostate tumor vs. wildtype (FIG. 4); b) Toremifene treated prostate histology vs. Placebo at 15 weeks (FIG. 5) Qualitatively, immunohistochemistry of Placebo and Toremifene treated tissues showed presence of T-antigen in the ventral prostate. Thus, the chemopreventive actity seen by Toremifene does not appear to be by suppression of the probasin promoter in the TRAMP model.

Conclusions: The ability of Toremifene to prevent the occurrence of prostate cancer in the TRAMP model has been confirmed utilizing more sensitive techniques to assess tumor fornation. The mechanism of Toremifene=s chemopreventive effects does not appear to be through loss of the transgene for the Large T-antigen protein.

EXAMPLE 6
Toremifene Induces Regression of Established Human Prostate Cancer Tumors in the Nude Mouse Model Prostate cancer currently remains the most commonly diagnosed cancer in American males. However, questions remain about the etiology and treatment of this disease especially is advanced forms. Hormone therapy remains the standard method of treatment for recurrent and advanced prostate cancer despite the common development of honnone refractory disease. Therefore, new approaches for the prevention and treatment of prostate cancer are needed to accommodate the increasing number of men diagnosed with this disease. The experiments and results below demonstrate that toremifene suppresses hormone sensitive LNCaP tumor growth in athymic nude mice.

Materials and Methods: One million LNCaP cells in Matrigel were subcutaneously injected into each flank of athyrnic nude mice. A total 40 mice were injected. After approximately 34 weeks, visible tumors developed. After recording the tumor size in two dimensions, the mice were divided into placebo and treatment groups based on equivalent tumor burden. A single pellet (placebo versus toremifene 35 mg) was subcutaneously implanted between the scapulae of each mouse. Weekly measurements of the tumor size were recorded. Tumor volume was calculated (tumor volume=05 (L+W)×L×W×0.5236, where L=tumor length and W=width). The tumor volume at the time of pellet implantation served as the point of reference for future comparison of that tumor=s size variation. The weekly variations of each tumor volume were recorded as percent differentiation from the original measurement at pellet implantation.

Figure 6:
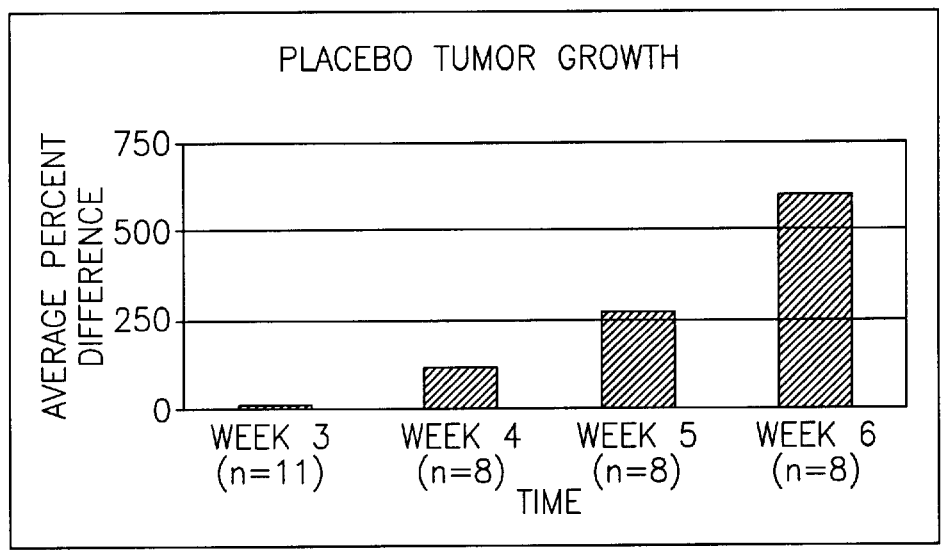
FIGS. 6A–6B: Comparison of placebo vs. Toremifene effects on tumor growth.
Figure 6:
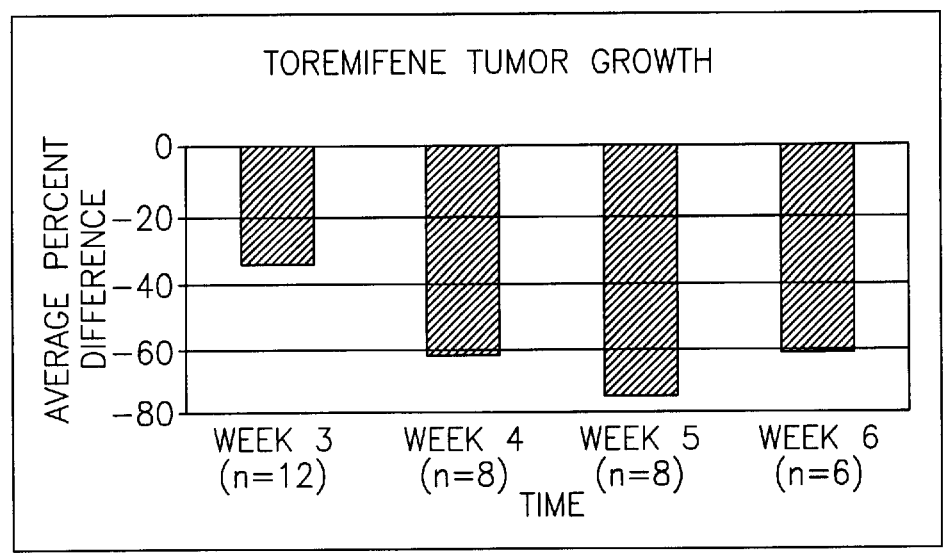

Results: Two mice died soon after pellet implantation due to mortal wounds from other mice. One mouse treated with tdremifene was excluded from the study due to excessive tumor hemorrhage and hematoma development. All mice developed visible tumors unilaterally or bilaterally. Each tumor was followed independently for the duration of the study. Twenty-four tumors were treated with lacebo and 28 tumors were treated with toremifene. The results are shown in Table 2 and FIGS. 6A and 6B.

TABLE 2

| Week N= | | % Change in volume relative to day 0 of treatment |
|---|---|---|
| | | PLACEBO GROUP |
| 3 | 11 | 9.44 |
| 4 | 8 | 115.27 |
| 5 | 8 | 271.71 |
| 6 | 8 | 600.88 |

TABLE 2-continued

| Week N= | | % Change in volume relative to day 0 of treatment |
|---|---|---|
| | | TOREMIFENE |
| 3 | 11 | −34.58 |
| 4 | 7 | −61.01 |
| 5 | 7 | −74.51 |
| 6 | 5 | −61.72 |

The follow-up interval will be extended on the currently reported population and data on additional animals are presently being collected.

Conclusion: Toremifene inhibits and induces regression of established LNCaP tumors. Although the mechanism by which toremifene exerts this effect is unknown, the ability to produce these effects supports the use of Toremifene as a treatment for prostate cancer and to prevent the recurrence of prostate cancer in high risk patients with established prostate cancer micrometastases.

EXAMPLE 7
The Role of Antiestrogens: Tamoxifen Citrate and Raloxifene (SERMs) and Faslodex (Pure Antiestrogen ICI 182, 780) in the prevention of Prostate Cancer Experimental design: Chemopreventive treatment of mice are initiated post-natal at 30 days. Three groups of 50 hybrid TRAMP male mice each are treated with either Tamoxifen citrate, or Raloxifene (SERMs) or Faslodex (pure antiestrogen ICI 182,780), The drugs is obtained as customized sustained-release pellets (Innovative Research of America, Sarasota, Fla.) and delivered as subcutaneous implants (see preliminary data). Control animals are receive placebo implant with no pharmacological activity. Animals (n=10) are sacrificed at periodic intervals, 10, 15, 20, 25 and 30 weeks age and the efficacy of the treatment leading to either absence of tumor formation or reduction in tumor size, if present, are assessed by comparison with placebo control animals. Blood is collected to evaluate changes in serum androgens and estrogens with each treatment. Prostatic tissues is saved for: a) morphometric studies; b) for histologic studies the tissue will be fixed in 10% buffered formalin, processed and paraffin embedded; c) for molecular studies the tissues is frozen in liquid nitrogen and stores at −70° C. Necropsies and survival data is alsd recorded.

The results of the experiment reveal the relative chempreventive efficacy of the various antiestrogens in the delay or prevention of prostate cancer in the TRAMP model. The morphological studies indicate the gross changes, if any, in the development of the prostate size and ductal pattern as a result of each treatment. The affinized tissue sections are stained using standard H&E techniques for histological changes such as PIN that will be assessed to monitor the appearance of precancerous lesions as a precuror of prostatic adencarcinoma. Serum estradiol and total testosterone levels are measured for each age interval to assess any changes in these hormones, and whether or not they correlate to changes in PIN. The peptide growh factor levels of TGF, TGF 1. TGF 3, and bFGF is quantitative in prostate samples taken at each interval. Corresponding peptide growth factor receptors is also assessed for EGFR and TGF RI and RII.

EXAMPLE 8
Toremifene causes Regression of HGPIN in a Phase IIa Prostate Cancer Chemoprevention Human Clinical Trial The chemopreventive effects of an antiestrogen, toremifene against prostate cancer have been reproducibly demonstrated herein in a well-established animal model of spontaneous human prostate cancer. This represents the first compound to demonstrate chemopreventive activity against prostate cancer. Moreover, High grade PIN (HGPIN) has been established and time tested as a precursor lesion for human prostate cancer also known as latent prostate cancer.

Consequently, HGPIN is used as an intermediate endpoint, or surrogate endpoint for human prostate cancer. In fact, the NCI has now recommended that PIN should be used as an intermediate endpoint, or surrogate endpoint for human prostate cancer.

A Phase IIa, open labeled non randomized single center study with 17 human subjects was conducted. In this protocol, patients with biopsy proven PIN are treated with 60 mg of Toremifene daily for 4 months. After 4 months, patients are rebiopsied and PIN status reassessed. Toremifene reduces PIN which thus will directly translate to a decrease in the incidence and a prolongation of the latency of prostate cancer. Other variables that are being investigated include serum PSA, quality of life issues, and prostatic expression of TGFβ1 expression (the presumed mechanism of action).

17 patients had high grade PIN. HGPIN was determined from 8 biopsies from biopsy session 1 which was confirmed 3 weeks later with repeat 8 prostate biopsy cores from biopsy session 2. After 4 months of Toremifene treatment (60 mg/day), the patients were subjected to prostate biopsy session of 8 prostate core biopsies from the same areas previously biopsied (left and right apex, midbase, base, and transition zones).

The pathological evaluation revealed complete resolution of PIN with atrophic changes in the prostatic epithelum. The patient experienced no acute or chronic toxicites while taking Toremifene. The serum PSA, serum free testosterone, serum total testosterone, and serum estradiol remained in the normal ranges. Quality of life was unchanged including no affect on potency and libido. Therefore, these results demonstrate a prostate chemopreventive role for the antiestrogen toremifene.

What is claimed is:

1. A method of suppressing or inhibiting latent prostate cancer of a subject comprising the steps of: administering to the subject a pharmaceutical composition comprising a compound having the formula:

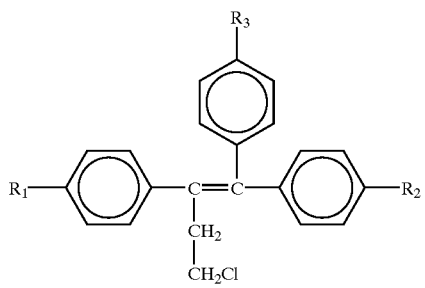

(I)

wherein $R_1$ and $R_2$, which can be the same or different, are H or OH; $R_3$ is $OCH_2CH_2NR_4R_5$, wherein $R_4$ and $R_5$, which can be the same or different, are H or an alkyl group of 1 to about 4 carbon atoms; and their pharmaceutically acceptable salts, esters, or N-oxides, and mixtures thereof.

2. A method of treating a subject with prostate cancer comprising the steps of: administering to the subject a pharmaceutical composition comprising a compound having the formula:

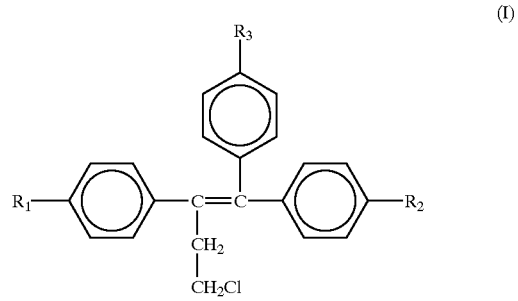

(I)

wherein $R_1$ and $R_2$, which can be the same or different, are H or OH; $R_3$ is $OCH_2CH_2NR_4R_5$, wherein $R_4$ and $R_5$, which can be the same or different are H or an alkyl group of 1 to about 4 carbon atoms; and their pharmaceutically acceptable salts, esters, or N-oxides, and mixtures thereof.

3. The method of any of claims 1 or 2, wherein the subject has a precancerous precursors of prostate adenecarcinoma.

4. The method of claims 3, wherein the precancerous precursors of prostate adenocarcinoma is prostate intraepithelial neoplasia (PIN).

5. The method of claim 4, wherein tee prostate intraepithelial neoplasia is high prostate intraepithelial neoplasia (HPIN).

6. The method according to any of claims 1 or 2, wherein said pharmaceutical composition fider comprises an acceptable carrier or diluent.

7. The method according to claim 6, wherein said carrier is selected from the group consistng of a gum, a starch, a sugar, a cellulosic material, or mixtures thereof.

8. The method according to claim 6, wherein said antiestrogen is administered subcutaneously, orally, intravenously, intraaterially, intramuscularly, or topically.

9. The method according to claim 6, whereby said subcutaneous administration is by implanting in said subject a pellet containing said pharmaceutical composition.

10. The method according to claim 9, wherein said pellet provides for controlled release of said phamaeutical preparation over a period of time.

11. The method according to claim 6, whereby said intravenous, intra-aertial, or intramuscular administeration is by intravenously, intraarterially, or intramuscularly injeating in said subject said pharmaceutical composition in a liquid form.

12. The method according to claim 6, whereby said oral administration is by orally admnistering to said subject in a liquid or solid preparation containing said pharmaceutical composition.

13. The method according to claim 6, whereby said topical administration is by applying to skin surface of said subject said pharmaceutical composition.

14. The method according to claim 3, wherein said pharmaceutical composition is selected from the group consisting of a pellet, a tablet, a capsule, a solution, a suspension, an emulsion, an elixir, a gel, a cream, and a suppository.

15. The method according to claim 14, wherein said suppository is a rectal suppository or a urethral suppository.

16. The method according to claim 6, wherein said pharmaceutical composition is a parenteral formulation.

17. The method according to claim 16, wherein said parenteral formulation comprises a liposome.

* * * * *